United States Patent [19]
Peterson

[11] 4,230,482
[45] Oct. 28, 1980

[54] HERBICIDE ANTIDOTES

[75] Inventor: Larry W. Peterson, Oakdale, Calif.

[73] Assignee: Shell Oil Company, Houston, Tex.

[21] Appl. No.: 41,288

[22] Filed: May 21, 1979

Related U.S. Application Data

[63] Continuation-in-part of Ser. No. 937,615, Aug. 28, 1978, abandoned.

[51] Int. Cl.$^3$ ................... A01N 25/32; A01N 43/70; A01N 43/36
[52] U.S. Cl. ............................................. 71/93; 71/95
[58] Field of Search ....................................... 71/93, 95

[56] References Cited

U.S. PATENT DOCUMENTS 3,620,710  11/1971  Schwarze .................................. 71/93

*Primary Examiner*—Catherine L. Mills

[57] ABSTRACT

The safety of the herbicide, cyanazine, with respect to grain sorghum, is improved by use of a selective antidote, which is a compound of the formula:

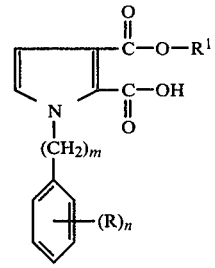

wherein the symbols have defined meanings.

5 Claims, No Drawings

HERBICIDE ANTIDOTES

This application is a continuation-in-part of application Ser. No. 937,619, filed on Aug. 28, 1978, abandoned.

BACKGROUND OF THE INVENTION

Cyanazine (2-chloro-4-(ethylamino)-6-(1-cyano-1-methylethylamino)-1,3,5-triazine) is used commercially as a herbicide. It is not generally satisfactory for controlling weeds in plantings of grain sorghum, since it tends to be rather toxic with respect to the sorghum plants at the dosages required to control the weeds.

DESCRIPTION OF THE INVENTION

It has been found that the phytotoxicity of the herbicide, cyanazine, with respect to grain sorghum plants, can be decreased, without significant reduction in its effectiveness with respect to controlling weeds, by use of an antidote, which is a compound of the formula:

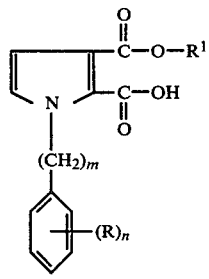

(I)

wherein m, n, R and $R^1$ are as follows:

| Compound No. | m | n | R* | $R^1$ |
|---|---|---|---|---|
| 1 | 0 | 0 | — | H |
| 2 | 1 | 0 | — | H |
| 3 | 0 | 1 | 3-(—CF$_3$) | H |
| 4 | 0 | 1 | 2-(—F) | H |
| 5 | 0 | 1 | 3-(—Cl) | H |
| 6 | 0 | 0 | — | —CH$_3$ |
| 7 | 0 | 1 | 2-(—Cl) | H |
| 8 | 1 | 1 | 3-(—Cl) | H |
| 9 | 0 | 2 | 2-(—Cl),5-(—Cl) | H |

*The number indicates the position of the substituent(s) on the indicated phenyl ring.

At the antidotally effective dosages, these antidotes are not phytotoxic to the sorghum plants.

Cyanazine can be applied pre-emergence or post-emergence, being taken up by the roots and foliage of the plants that it contacts.

Depending upon the way(s) the antidote and herbicide are applied, the antidote is applied at, or before, the time the herbicide is applied, the essential requirement being that the antidote be present in the sorghum plant a sufficient time before the herbicide contacts the plant to provide the antidotal effect. Thus, the antidote can be applied to the sorghum seeds, and the herbicide applied at the time the seeds are planted, or afterwards, either before or after the sorghum plant's foliage has emerged from the soil. Also, since the antidote passes through the soil more rapidly than does the herbicide, the antidote can be applied to the soil in which the sorghum seeds are to be planted at, or before, or after, the time the sorghum seeds are planted therein and before the sorghum plant's foliage has emerged from the soil and the herbicide applied at the time the seeds are planted, or afterwards, either before or after the sorghum plant's foliage has emerged from the soil. Further, both the antidote and the herbicide can be applied after the sorghum plant's foliage has emerged from the soil. However, in this case, the herbicide is absorbed very rapidly by the sorghum plant, so that the antidote must be applied at least one day, and preferably two to three days before the herbicide is applied, to permit the antidote to provide the antidotal effect before the herbicide is applied. To avoid this sequential application of the antidote and the herbicide, and to minimize any possibility of toxicity of the antidote to the sorghum plants, such post-emergent treatment is less attractive than pre-emergence treatment.

To summarize, as a general matter, to provide the antidotal effect, the antidote must be available to the growing sorghum plant just before the plant is contacted with the herbicide. The available evidence appears to show that the antidote is most effective when in the soil environment of the sorghum plants prior to the time the sorghum seeds have sprouted, whether the herbicide is applied before or after the foliage of the sorghum plant has emerged from the soil. When applied to the soil, the antidote can be placed on the surface of the soil and incorporated into the soil by water (by rain or irrigation techniques) or it can be incorporated in the soil by mixing techniques.

The amount of the antidote that is required will depend upon the way in which it is applied. When applied to the sorghum seeds, the suitable dosage of the antidote is from about 0.25 to about 5, and usually from about 0.5 to about 3, percent of the weight of the seed. When applied to the soil, the suitable dosage of the antidote is from about 0.5 to about 5, usually about 1 to about 4, pounds per acre when applied pre-emergence, and from about 0.25 to about 2, usually about 0.5 to about 1.5, pounds per acre, when applied post-emergence. Since the antidote does not significantly reduce the effectiveness of the herbicide with respect to the weeds to be controlled, the herbicide can be used at the dosages ordinarily recommended.

Whereas the antidote can be used neat it is ordinarily desirable from the standpoint of effectiveness of application to employ it in the form of a formulation containing in addition to the antidote, one or more materials which enable the antidote to be used most efficiently in a given technique for its application.

Thus, when the antidote is to be coated on sorghum seed, it usually will be found to be desirable to dissolve it in a suitable non-phytotoxic solvent and treat the seeds with the solution, or to mix it with a suitable liquid or solid carrier for treatment of the seed. An adhesive or sticker, such as methyl cellulose, may aid in the formation of a stable coating. Such techniques, as well as techniques for physically effecting the coating, are well known in the art, and may be used to apply antidotes of this invention to sorghum seeds.

For application of the antidotes to soil and/or the foliage of the sorghum plants, the antidotes can be formulated using any of the adjuvants conventionally used in the art, and applied by conventional techniques.

The term "adjuvant" as used herein means a material, which may be inorganic or organic and of synthetic or natural origin, with which the antidote is mixed or formulated to facilitate its application to the plant, seed or soil, or its storage, transport and/or handling. The adjuvant may be a solid or a liquid.

Suitable solid adjuvants are the non-phytotoxic solid carriers conventionally used for application of agricultural chemicals.

Suitable liquid adjuvants include non-phytotoxic solvents for antidotes and non-phytotoxic liquids in which the antidote is insoluble or only slightly soluble.

The formulation suitably can contain one or more surface-active agents. The surface-active agent may be an emulsifying agent or a dispersing agent or a wetting agent. It may be nonionic or ionic. Surface-active agents usually applied in formulating agricultural chemicals are suitable.

The antidotes may be formulated as a wettable powder, as a dust, as granules, solution, emulsifiable concentrate, emulsion, suspension concentrate or aerosol, as convenient for the intended application. Encapsulated formulations and controlled release formulations also are contemplated.

The formulation suitably can also contain other materials, such as dispersing agents, suspending agents such as protective colloids, and thixotropic agents, defoamers, corrosion inhibitors, stabilizers, penetrants and stickers. Certain organic additives or inorganic salts may be dissolved in the carrier to assist in preventing sedimentation or as antifreeze agents.

Aqueous dispersions and emulsions, for example, compositions obtained by diluting a wettable powder or an emulsifiable concentrate with water, are suitable.

The formulations of the antidote may also contain other ingredients, for example, other compounds possessing insecticidal, nematocidal, fungicidal and/or bactericidal properties.

As a class, the antidotes are known compounds. Thus, Compound 1 is disclosed in Huisgen and Laschtuvka, Chemische Berichte, 93, 65-81 (1960), and was prepared by the method shown therein. The other antidotes were prepared as follows (in all cases, the identities of the products, and intermediates, involved were confirmed by appropriate elemental and spectral analyses):

1-(Phenylmethyl)-1H-pyrrole-2,3-dicarboxylic acid (2)

3.8 g of sodium hydride (50% in mineral oil) was added in portions at 25° C. to a stirred solution of 13.7 g of the dimethyl ester of 1H-pyrrole-2,3-dicarboxylic acid (Rapoport and Willson, *J. Organic Chemistry*, 26, 1102-1104 (1961) in 70 ml of N,N-dimethylacetamide. After one hour, 9.5 g of benzyl chloride was added drop-by-drop over a 10 minute period, at 25°-30° C. The resulting mixture was stirred overnight at 25° C. and then was poured into 300 ml of water. The mixture was extracted with methylene chloride. The extract phase was isolated, the solvent was evaporated and the residue was dry column chromatographed over silica gel, using a 4:16:80 by volume mixture of tetrahydrofuran, ethyl acetate and n-hexane as eluent. The product was an oil, identified as the dimethyl ester of 1-(phenylmethyl)-1-H-pyrrole-2,3-dicarboxylic acid (2A).

A mixture of 5.4 g of (2A), 4.0 g of sodium hydroxide and 40 ml of water was stirred and refluxed for 22 hours. The mixture was cooled, and acidified with 20 ml of 6 N hydrochloric acid. Recrystallization of the resulting solid product from a mixture of acetone and pentane gave 2, m.p.: 182°-184° C.

1-(3-Trifluoromethylphenyl)-1H-pyrrole-2,3-dicarboxylic acid (3)

A mixture of 18.9 g of the diethyl ester of 3,6-dicyano-2,7-dihydroxy-2,4,6-octatrienedioic acid (Huisgen and Laschtuvka, supra), 20.0 g of 3-trifluoromethylaniline and 150 ml of dry toluene was stirred at reflux for 3 hours, water of reaction being distilled from the mixture as it was formed. The resulting mixture was filtered and the solvent was evaporated under reduced pressure. The residue was dissolved in 50 ml of hot ethanol and the solution was chilled in a refrigerator. The resulting solid was filtered and recrystallized from ethanol to give the ethyl ester of 3-cyano-1-((3-trifluoromethyl)phenyl)-1H-pyrrole-2-carboxylic acid (3A), m.p.: 77°-79° C.

5.1 g of 3A in 50 ml of ethanol was mixed with 2.6 g of sodium hydroxide in 10 ml of water and the mixture was stirred and refluxed for 24 hours. Solid which formed on the walls of the reactor was dissolved by adding water and the mixture was refluxed for 2 hours. The mixture was cooled, water was added and the ethanol removed under reduced pressure. The residue was acidified with 6 N hydrochloric acid, chilled in ice and filtered. The solid was washed with water and dried, then was recrystallized by boiling it in 50 ml of dimethyl ketone, filtering the hot mixture, adding pentane to the hot filtrate until it was cloudy then storing it in a freezer, and separating the solid (3). More pentane was added to give a second crop of 3. 3 was a solid, m.p.: 198°-199° C. (with decomposition).

1-(3-Chlorophenyl)-1H-pyrrole-2,3-dicarboxylic acid (5)

A mixture of 9.2 g of the diethyl ester of 3,6-dicyano-2,7-dihydroxy-2,4,6-octatrienedioic acid, 7.0 g of 3-chloroaniline and 75 ml of dry toluene was stirred at reflux for 3 hours, water of reaction being distilled from the mixture as it was formed. The resulting mixture was filtered and the solvent was evaporated under reduced pressure. The residue was dissolved in 35 ml of hot ethanol and the solution was chilled in a freezer. The resulting solid was filtered and dried under vacuum to give the ethyl ester of 3-cyano-1-(3-chlorophenyl)-1H-pyrrole-2-carboxylic acid (5A), m.p.: 113°-116° C.

5.1 g of 5A in 10 ml of ethanol was mixed with 3.0 g of sodium hydroxide in 30 ml of water and the mixture was stirred and refluxed for 66 hours. The mixture was cooled, and acidified with 20 ml of 6 N hydrochloric acid. The solid was filtered, rinsed with water, and dissolved in acetone. The solution was filtered, the filtrate was concentrated, mixed with water and the mixture was placed in a freezer. The solid was filtered and vacuum dried to give 5, m.p.: 214°-215° C. (with decomposition).

The other antidotes were prepared in a similar manner:

| Compound | Melting Point (°C.) |
| --- | --- |
| 4 | 215-217* |
| 7 | 210-212* |
| 8 | 200-201* |
| 9 | 105-110* |

*with decomposition

3-Methyl ester of
1-phenyl-1H-pyrrole-2,3-dicarboxylic acid (6)

A mixture of 2.1 g of 1-phenyl-1H-furo(3,4-b)-pyrrole-4,6-dione (Huisgen and Laschtuvka, supra) and 50 ml of methanol was stirred and refluxed for four hours. The excess methanol was evaporated under reduced pressure and the residue was dissolved in a mixture of diethyl ether and methylene chloride. The solution was filtered, a small amount of pentane was added and the mixture was cooled in a freezer. Solid which formed was filtered and dried under reduced pressure at 50° C. to give 6, m.p.: 131°–134° C.

The usefulness of these compounds to ameliorate the effect of cyanazine with respect to grain sorghum was established as follows:

Example 1

Grain sorghum seeds (Pioneer 828) were planted in 4-inch pots, in sand as growth medium, and were watered with one-quarter strength Hoagland's solution (D. R. Hoagland D. I. Arnon, The Water Culture Method for Growing Plants Without Soil, Circular 347, University of California). After one week of growth under continuous light, the seedlings were watered for two days with the Hoagland's solution containing the test compound at (a) 3 and (b) 0.3 micrograms per milliliter. On the following two days, the plants were watered with Hoagland's solution containing BLADEX ® Herbicide (containing approximately 80% by weight of cyanazine) to provide 0.5 or 1.5 micrograms of cyanazine per milliliter of solution. The higher dosage of cyanazine was deliberately chosen for causing complete death of the sorghum plants, with the lower dosage being sufficient to cause severe damage to the plants. Two weeks later, the plants then were visually checked and the damage was rated on a scale of zero to nine, zero indicating no observable effect and nine indicating complete death of the plants. The results are set forth in Table I.

TABLE I

| Dosage of Test Compound (μg/ml) | 3.0 | 0.3 | 0 | 3.0 | 0.3 | 0 |
|---|---|---|---|---|---|---|
| Dosage of Cyanazine (μg/ml) | 1.5 | 1.5 | 1.5 | 0.5 | 0.5 | 0.5 |
| Compound No. | | | | | | |
| 1 | 9 | 9 | 9 | 2 | 4 | 7 |
| 2 | 6 | 8 | 9 | 2 | 3 | 6 |
| 3 | 6 | 9 | 9 | 1 | 1 | 7 |
|   | 8 | 9 | 8 | 3 | 3 | 6 |
| 4 | 5 | 9 | 9 | 1 | 7 | 7 |
|   | 8 | 9 | 9 | 4 | 5 | 7 |
| 5 | 8 | 9 | 9 | 3 | 4 | 7 |
| 6 | 6 | 9 | 9 | 1 | 1 | 7 |
|   | 9 | 9 | 8 | 4 | 3 | 6 |
| 7 | 7 | 8 | 9 | 1 | 2 | 6 |
|   | 8 | 7 | 8 | 6 | 5 | 6 |
| 8 | 9 | 9 | 9 | 3 | 4 | 7 |
| 9 | 9 | 9 | 9 | 3 | 3 | 7 |

In this test, a reading of 7 or 8 is considered to be an indication of a safening effect, compared to a reading of 9.

EXAMPLE 2

Grain sorghum seeds (Pioneer 828) were planted in sandy loam soil in pots. One series of pots was treated with Compounds 1, 2, 4, 5, 6 and 7 only, one series with BLADEX Herbicide only and one series with a combination of BLADEX Herbicide and one each of the various compounds. The herbicide was formulated as a wettable powder containing approximately 80% by weight of cyanazine. Compounds 1, 2, 4, 5, 6 and 7 were applied as a solution in a non-phytotoxic standard solvent, to provide a dosage of Compounds 1, 2, 4, 5, 6 and 7 of 3 pounds/acre.

The plants were watered and held under identical conditions. When the plants were at the second true leaf stage, the herbicide was applied, as a solution in the standard solvent, with a sprayer that varied the dosage logarithmically from 0.5 to 5 pounds of cyanazine/acre, over the series of pots that were sprayed. The plants then were watered and all of the pots held under identical conditions. After 14–21 days the condition of the plants was observed, and the dosages (pounds/acre) that caused 10% and 90% kill of the plants, respectively, was determined, these being designated as the $GI_{10}$ and $GI_{90}$ dosages, respectively. The results of the test are summarized in Table II.

TABLE II

| Treatment | Dosage | |
|---|---|---|
|  | $GI_{10}$ | $GI_{90}$ |
| Check (No Treatment) | Plants normal. | |
| Compound 1 only | Some anthocyanin spotting, growth normal. | |
| Compound 2 only | Some anthocyanin spotting, growth normal. | |
| Compound 4 only | Some anthocyanin spotting, growth normal. | |
| Compound 5 only | Some anthocyanin spotting, growth normal. | |
| Compound 6 only | Some anthocyanin spotting, growth normal. | |
| Compound 7 only | Some anthocyanin spotting, growth normal. | |
| Herbicide only | <0.5 | 0.5 |
| Compound 1 + Herbicide | 0.5 | 1.0 |
| Compound 2 + Herbicide | 0.5 | 2.5 |
| Compound 4 + Herbicide | 0.6 | 1.9 |
| Compound 5 + Herbicide | 1.3 | 2.1 |
| Compound 6 + Herbicide | 0.8 | 1.3 |
| Compound 7 + Herbicide | 0.7 | 2.0 |

EXAMPLE 3

A series of tests were conducted by the procedures described in Example 2, the herbicide being applied pre-emergence, and compounds 1, 2, 4, 5, 6 and 7 being applied pre-emergence. The results were reported as $GI_{10}$ and $GI_{90}$ dosages in pounds/acre and are recorded in Table III.

TABLE III

| Treatment | Dosage | |
|---|---|---|
|  | $GI_{10}$ | $GI_{90}$ |
| Compound 1 + Herbicide | 1.0 | 2.1 |
| Compound 2 + Herbicide | 0.8 | 1.5 |
| Compound 4 + Herbicide | 1.0 | 1.9 |
| Compound 5 + Herbicide | 0.9 | 1.5 |
| Compound 6 + Herbicide | 0.9 | 1.5 |
| Compound 7 + Herbicide | 0.7 | 1.6 |
| Herbicide Only | 0.5 | 0.8 |

EXAMPLE 4

To see if Compound 6 might moderate cyanazine activity with respect to weeds, the following tests were made. Various weed seeds were planted in sandy loam soil in pots. One series of pots was treated with Compound 6; a second series was treated with Compound 6, then with cyanazine; a third series was treated with cyanazine only, and a fourth series was left as an untreated check. Compound 6 was applied uniformly at 2 pounds per acre while cyanazine was applied at dosages that varied logarithmically from 0.1 to 1.0 pounds per acre over the pots. After 2½ weeks under identical growing conditions, all of the plants were observed, and the dosage (pounds per acre) that would kill 90% of the plants was determined. The results of the test are summarized in Table IV. As can be seen therefrom, Compound 6 did not adversely affect the herbicidal activity of cyanazine with respect to any of the weeds.

TABLE IV

| Species | Cyanazine | | Cyanazine + Compound | | Compound 6 | | Check | |
|---|---|---|---|---|---|---|---|---|
| | $GI_{90}$ | $GI_{10}$ | $GI_{90}$ | $GI_{10}$ | $GI_{90}$ | $GI_{10}$ | $GI_{90}$ | $GI_{10}$ |
| Watergrass | 0.15 | <0.1 | 0.15 | <0.1 | $-^a$ | — | — | — |
| Crabgrass | 0.15 | <0.1 | 0.15 | <0.1 | $b$ | $b$ | — | — |
| Downy brome | 0.12 | <0.1 | 0.12 | <0.1 | — | — | — | — |
| Pigweed (red root) | 0.2 | 0.12 | 0.25 | 0.15 | — | — | — | — |
| Sicklepod | 0.3 | 0.25 | 0.4 | 0.25 | — | — | — | — |
| Mustard | <0.1 | <0.1 | <0.1 | <0.1 | — | — | — | — |

$^a$— indicates that no effect was observed.
$^b$some inhibition of adventitious root growth was observed.

From the results of tests on chemically closely related antidotes (application Ser. No. 41,266), it is believed that the effectiveness of the antidotes of this invention will differ from variety to variety of grain sorghum: with respect to most varieties, the antidote will significantly reduce the toxicity of cyanazine, but in some cases it will have no significant effect. From the tests that have been conducted, it is believed that the related antidotes and the antidotes of this invention have very similar biological properties and act in a very similar manner. It has been noted that with respect to many varieties of grain sorghum, application of one of the related antidotes results in the formation of red spots, on the foliage of the plant, which are believed to result from the formation of anthocyanins. It has been further noted that in general, the related antidotes appear to be effective with respect to those varieties of sorghum which become spotted when the antidote is applied to the plant, and appear to be ineffective with respect to those varieties of sorghum which do not become spotted when the antidote is applied. However, about 10-15% of the varieties tested did not follow this pattern, i.e., some varieties formed the spots, but the antidote was not effective; some did not form the spots, but the antidote was effective. At the present time, the applicant does not have an explanation for these phenomena. Because of the similarity of the related antidotes, it is believed that the antidotes of this invention will have similar properties.

In any case, it is a simple matter to ascertain whether an antidote of this invention is effective, with respect to any particular variety of grain sorghum, by testing the variety according to the procedure described in Example 1, supra.

I claim:

1. A method for increasing the safety of the herbicide, cyanazine, with respect to a grain sorghum plant, which comprises providing the growing sorghum plant, at the time it is contacted with the herbicide, with an effective amount of an antidote compound of the formula:

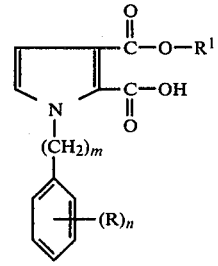

wherein m, n, R and $R^1$ are as follows:

| Compound No. | m | n | R | $R^1$ |
|---|---|---|---|---|
| 1 | 0 | 0 | — | H |
| 2 | 1 | 0 | — | H |
| 3 | 0 | 1 | 3-(—$CF_3$) | H |
| 4 | 0 | 1 | 2-(—F) | H |
| 5 | 0 | 1 | 3-(—Cl) | H |
| 6 | 0 | 0 | — | —$CH_3$ |
| 7 | 0 | 1 | 2-(—Cl) | H |
| 8 | 1 | 1 | 3-(—Cl) | H |
| 9 | 0 | 2 | 2-(Cl),5-(—Cl) | H |

2. A method according to claim 1 wherein the antidote compound is applied to the grain sorghum seed before it is planted.

3. The seed produced by the method of claim 2.

4. A method according to claim 1 wherein the antidote compound is introduced into the soil before the sorghum seed is planted therein.

5. A method according to claim 1 wherein the antidote compound is introduced into the soil wherein the sorghum plant is growing.

* * * * *